United States Patent
Blumstein et al.

(10) Patent No.: US 9,808,638 B2
(45) Date of Patent: Nov. 7, 2017

(54) ACTIVE IMPLANTABLE MEDICAL DEVICE WITH CARDIAC LEAD AND PERIPHERAL LEAD DISCRIMINATION

(71) Applicant: SORIN CRM SAS, Clamart (FR)

(72) Inventors: Hervé Blumstein, Mévoisins (FR); Hervé Mével, Chastre (BE)

(73) Assignee: SORIN CRM SAS, Clamart (FR)

(*) Notice: Subject to any disclaimer, the term of this patent is extended or adjusted under 35 U.S.C. 154(b) by 0 days.

(21) Appl. No.: 14/945,171

(22) Filed: Nov. 18, 2015

(65) Prior Publication Data
US 2016/0136445 A1     May 19, 2016

(30) Foreign Application Priority Data
Nov. 19, 2014   (FR) ...................... 14 61187

(51) Int. Cl.
| A61N 1/00 | (2006.01) |
| A61N 1/39 | (2006.01) |
| A61N 1/36 | (2006.01) |
| A61N 1/362 | (2006.01) |
| A61N 1/368 | (2006.01) |
| A61N 1/37 | (2006.01) |
| A61N 1/05 | (2006.01) |
| A61N 1/08 | (2006.01) |

(52) U.S. Cl.
CPC .......... *A61N 1/3962* (2013.01); *A61N 1/362* (2013.01); *A61N 1/3605* (2013.01); *A61N 1/3686* (2013.01); *A61N 1/37* (2013.01); *A61N 1/0551* (2013.01); *A61N 1/36114* (2013.01); *A61N 1/3702* (2013.01); *A61N 2001/083* (2013.01)

(58) Field of Classification Search
CPC .............................. A61N 1/3962; A61N 1/3605
USPC ............................................................ 607/40
See application file for complete search history.

(56) References Cited

U.S. PATENT DOCUMENTS

| 5,330,507 A | 7/1994 | Schwartz |
| 5,374,279 A | 12/1994 | Duffin et al. |
| 6,317,633 B1 | 11/2001 | Jorgenson et al. |

(Continued)

FOREIGN PATENT DOCUMENTS

| EP | 0 686 407 A1 | 12/1995 |
| EP | 1 618 923 A1 | 1/2006 |

(Continued)

OTHER PUBLICATIONS

Preliminary Search Report for French Patent Application No. 1461187, dated Mar. 31, 2015, 1 page.

(Continued)

*Primary Examiner* — Nadia A Mahmood
(74) *Attorney, Agent, or Firm* — Foley & Lardner LLP (57) ABSTRACT

The device includes a cardiac therapy circuit with a first terminal, and a peripheral therapy circuit with a second terminal. These terminals can either receive a cardiac detection/stimulation lead or a peripheral detection/stimulation lead of an organ. The device is configured to recognize the leads and automatically configure the connection terminals according to the type of lead received by the terminal. This includes discrimination methods for identifying the terminal on which a cardiac signal is detected, and selectively activating the cardiac therapy circuit and the peripheral therapy circuit based on the detection of the cardiac signal on a lead.

12 Claims, 7 Drawing Sheets

(56) References Cited

U.S. PATENT DOCUMENTS

| | | |
|---|---|---|
| 8,527,045 B2 | 9/2013 | Krause et al. |
| 2006/0004420 A1 | 1/2006 | Rossing et al. |
| 2010/0114221 A1* | 5/2010 | Krause ............... A61N 1/36114 607/7 |
| 2010/0137929 A1* | 6/2010 | Libbey ................. A61N 1/3752 607/5 |
| 2011/0224988 A1 | 9/2011 | Mahajan et al. |
| 2012/0123496 A1 | 5/2012 | Schotzko et al. |
| 2012/0197331 A1 | 8/2012 | Germanson et al. |
| 2013/0116743 A1 | 5/2013 | Karamanoglu et al. |
| 2014/0330328 A1 | 11/2014 | Christie et al. |

FOREIGN PATENT DOCUMENTS

| | | |
|---|---|---|
| EP | 2 092 885 A1 | 8/2009 |
| EP | 2 179 764 A1 | 4/2010 |
| EP | 2 402 054 A1 | 1/2012 |
| EP | 2 564 896 A1 | 3/2013 |
| FR | 2558732 | 8/1985 |

OTHER PUBLICATIONS

Preliminary Search Report for French Patent Application No. 1461188, dated Apr. 15, 2015, 2 pages.

\* cited by examiner

ACTIVE IMPLANTABLE MEDICAL DEVICE WITH CARDIAC LEAD AND PERIPHERAL LEAD DISCRIMINATION

CROSS-REFERENCE TO RELATED PATENT APPLICATIONS

This application claims the benefit of and priority to French Patent Application No. 1461187, filed Nov. 19, 2014, which is incorporated herein by reference in its entirety.

BACKGROUND

The invention relates to active implantable medical devices, as defined by Directive 90/385/EEC of 20 Jun. 1990 of the Council of the European Communities.

These devices include an implantable generator containing in a housing various electronic circuits, a battery and a connector head for the coupling of the generator to various leads provided with electrodes for detecting electrical potentials at a remote location and/or for delivering stimulation pulses.

At the time of implantation, the leads are mechanically connected and electrically connected to the generator via plug sockets that are inserted into the connector of the generator so as to connect different contacts of these plugs to homologous terminals of the internal circuit of the generator.

The leads may be leads directly and separately connected to the generator, as well as indirectly connected by an intermediate accessory connecting various leads to a common, multipolar connector of the generator. Each of the leads are connected to internal terminals of the circuit of the generator, the circuit having the same number of terminals as the number of leads, or the electrodes of the leads.

The disclosure relates more particularly to those devices which enable both:
by one or more intracardiac or epicardial "cardiac" leads, detection of depolarization potentials of the myocardium ("cardiac potentials") and/or to deliver to the heart electrical stimulation, defibrillation or resynchronization pulses ("cardiac pacing pulses"). These functions of detection and/or delivery of pulses in relation with the heart will hereinafter be collectively referred to as "cardiac therapy." The documents US 2010/137929 A1, EP 2402054 A1, U.S. Pat. No. 6,317,633 B1, FR 2,558,732 A1, US 2012/123496 A1 and US 2011/224988 A1 describe examples of such devices, which may include a plurality of cardiac detection/stimulation leads provided with electrodes located in or on the heart; and
by one or more "peripheral leads" implanted on a "peripheral anatomical structure" (e.g., organ) other than the heart, to detect depolarization potentials ("peripheral" potentials) and/or to issue to the peripheral anatomical structure stimulation pulses ("peripheral" pulses). The peripheral pulses may be different from those delivered to the heart both by their nature and their sequencing. These functions of detection and/or delivery of pacing pulses in relation to the peripheral anatomical structures will hereafter be collectively referred to as "peripheral therapy."

The peripheral anatomical structure may be, for example and without limitation, a nerve, especially the vagus nerve, the brain, a muscle, etc. The therapy device can be in particular, and without limitation, stimulation therapy to the vagus nerve (VNS), stimulation of the spinal cord (SCS), deep brain stimulation (DBS), stimulation of a peripheral nerve (PNS), carotid stimulation (CBS), muscle stimulation (MS), etc. Direct stimulation of the nervous system is often referred to as neuromodulation.

EP 2179764 A2 describes such a device capable of delivering two therapies of different nature simultaneously, from respective stimulation channels, which may optionally be grouped in the same generator housing.

Such a device requires at least two leads which are also of different nature (one or more lead(s) for the cardiac therapy and one or more other lead(s) for the peripheral therapy).

For practical reasons, it may be desirable to have identical connectors for all of the leads connected to the generator, irrespective of their function. The availability of identical connectors, for example IS-1 connectors, simplifies the design of the generator and of the leads, to optimize the usability by using already available leads, etc.

This method therefore introduces a risk of incorrect placement of leads within the generator plugs during the implantation procedure. In the case of lead connection error, the cardiac pacing pulses and peripheral stimulation delivered by the generator will be applied to the wrong target (the heart instead of the peripheral anatomical structure and vice versa), or will not be applied at all. The lead connector error may present risks for the patient. For example, when a peripheral therapy is applied to the heart, the therapy could induce tachycardia or even fibrillation depending on the energy and frequency of the delivered pulses.

There are various known generators able to automatically detect the insertion of a lead and to subsequently activate various features, initialize a number of parameters, store initial data for implantation, etc.

These devices typically operate by measuring the impedance between the generator terminals of the connector. In the absence of a lead this impedance is very high, but upon insertion of a lead, the value decreases below a certain threshold, the crossing of the threshold is detected causing the generator to change the mode of operation of the pacemaker from a standby mode to a fully functional mode.

A continuous scan of the impedance, however, is disadvantageous in terms of consumption and lifetime of the battery, because it requires, at each measurement, the injection of current and the activation of circuits for measuring the corresponding collected voltage. It is therefore not desirable to operate a continuous scan, particularly in the commercial use of the generator. Moreover, the use of an automatic impedance measurement for certain peripheral leads may be undesirable.

EP 1618923 A1 (Sorin CRM) discloses another technique of detecting a lead, which does not require the direct and continuous measurement of the impedance between the terminals of the generator. This technique is only to monitor the consumption of the device. Any modification of the consumption revealing a change in behavior of the device, is generally due to the connection of a lead and the implantation of the lead due to: i) stimulation on a charge that is no longer infinite (as was the case in the commercial use), ii) detection of cardiac signals activating the digital filters whose consumption depends on the input signal, and iii) wake-up of microcontroller running specific software instructions on each new detection. The device described in EP 1618923 A1 also determines the type of lead used (monopolar or bipolar) and automatically adapts the various circuits and algorithms of the device according to the type of lead. This function minimizes any risk of error resulting in a defect which may, for example, cause the application of a bipolar stimulation to a monopolar lead.

However, this device, which is based on the specificities of cardiac leads and signals, cannot be applied to a mixed generator capable of delivering both a cardiac therapy and a peripheral therapy. The two targets (heart and peripheral anatomical structure) are very different in nature. The cardiac therapy generator could distinguish a bipolar cardiac lead from a monopolar cardiac lead, but may not be able to tell the difference between a cardiac lead and a peripheral lead, or between a peripheral lead and the absence of a lead. The device could also tell the difference between an absence of lead and the presence of a lead (by the impedance measurement), but would not know if the lead is a cardiac lead or a peripheral lead.

The technique described in EP 1618923 A1 is limited to the verification of the connection of leads and to the correct setting of the generator depending on the type (monopolar or bipolar) of lead. It does not restore as appropriate a misconfiguration, or does not leave the option for the practitioner to connect the leads of various natures to the generator in a completely interchangeable method, while leaving the latter to automatically establish the correct connection scheme, irrespective of the manner in which leads were inserted on the generator.

SUMMARY

Generally, the disclosure relates to an active implantable medical device capable of delivering both a cardiac therapy and a peripheral therapy. The device may eliminate risks associated with a faulty connection of leads and/or detect such faulty connection.

In a first embodiment, a device which verifies, at the time of implantation, the compatibility of the leads connected to the generator, before initiating any therapy. In case of an error in the lead connection, the generator inhibits delivery of peripheral and/or cardiac therapies. Preferably, the inhibited therapy will be the peripheral therapy. The cardiac therapy may be inhibited if the amount of energy delivered by the generator of cardiac therapy may induce side or adverse effects in the patient if the cardiac pulses are applied to the peripheral device.

In a second embodiment, a device capable of detecting which lead is connected to which circuit (e.g., which lead is connected to the cardiac therapy circuit) and capable, in response, of automatically ensuring the correct coupling of the leads to the corresponding circuits (e.g., say of the cardiac lead to the cardiac therapy circuit and of the peripheral lead to the peripheral therapy circuit). This allows leads to have identical connection plugs, without the need for the practitioner to check which of the plugs should be inserted into a specific generator. The device mitigates the risk of poor compatibility of the connection of the leads by an auto-detection of leads and automatic configuration of the connection pattern of the leads to the generator terminals associated with them.

According to the aforementioned first aspect, the invention provides a device including, in a manner known per se from EP 2179764 A2 cited above:
A cardiac therapy circuit, including a module for detection of first potentials and for pacing, defibrillation and/or resynchronization pulse generation of a heart;
A peripheral therapy circuit, including a module for detection of second potentials and for generation of peripheral stimulation pulses;
At least a first connection terminal, adapted for receiving a detection/stimulation implantable lead in or on the heart; and
At least one second connection terminal, suitable for receiving a detection/stimulation implantable lead on or near a peripheral anatomical structure located remotely from the heart.

In some embodiments, each of said first and second connection terminals is adapted to receive either one or the other of said lead in or on the heart and said other lead on or near a peripheral anatomical structure, and the device further verifies the respective connection configuration of said leads to said terminals, the verification including:
a) collecting a signal on said first connection terminal and analyzing the collected signal to reveal the presence of a cardiac signal,
b) collecting a signal on said second connection terminal and analyzing the collected signal to reveal the presence of a cardiac signal,
c) if the criterion a) is verified and the criterion b) is not verified, issue in response an activation control to the cardiac and peripheral therapy circuits, and
d) if one and/or the other of the criteria a) and b) is not verified, outputting in response an inhibit control to the cardiac and peripheral therapy circuits.

According to various advantageous subsidiary embodiments:
The verification further includes transmitting an alert signal if one and/or the other criteria a) and b) is not verified;
The verification further includes transmitting a confirmation signal if either criteria a) and b) are verified;
The verification further includes testing a level of the collected signal on one and the other of the first or on the second connection terminal, to reveal the presence of a cardiac signal. The presence of a cardiac signal may be revealed if the signal level received on the terminal exceeds a given threshold over a duration of a predetermined detection window;
The testing of the signal further includes a stability test of intervals separating successive events of said cardiac signal collected during the period of the detection window, the stability test outputting an indicator of stability or lack of stability. In addition, the verification further includes supplying, in response, an inhibit control to the cardiac therapy circuitry and to the peripheral therapy circuitry if the issued indicator is an indicator of lack of stability;
The verification further includes comparing the levels, determined by the level test, of signals respectively collected on the first and second terminals. In addition, the comparison further includes supplying, in response, an inhibit control to the cardiac therapy circuitry and to the peripheral therapy circuitry if the difference between the respective levels of the signals collected on the first and second terminals is less than a predetermined minimum difference.

According to the aforementioned second embodiment, the invention provides a device including, in a manner known per se from EP 2179764 A2 cited above:
A cardiac therapy circuit including a module for detection of first potentials and for generation of pacing, defibrillation and/or resynchronization pulses to the heart;
A peripheral therapy circuit, including a module for detection of second potentials and for generation of peripheral stimulation pulses;
At least a first connection terminal adapted to receive a lead; and
At least a second connection terminal adapted to receive another lead.

In some embodiments, one of the leads is a detection/stimulation lead implantable in or on the heart and the other is a detection/stimulation lead implantable on or near a peripheral anatomical structure remotely located from the heart.

In some embodiments, each of said first and second connection terminals is adapted to receive either one or the other of said lead and other lead, and the device further includes methods of recognition of said leads and of automatic configuration of terminals, including:

Discriminating methods, adapted to:
  collect a signal on one of the first and second connection terminals;
  analyze the collected signal to reveal the presence or absence of a cardiac signal; and
  deliver in response an identification of the one among the first and second connection terminals on which the presence of a cardiac signal was proved; and Switching methods, operating in response to the discriminating methods for:
  coupling the cardiac therapy circuit to the connection terminal identified by the discriminating methods as being that on which the presence of a cardiac signal was identified; and
  coupling the peripheral therapy circuit to the other connection terminal.

According to various advantageous subsidiary embodiments:

The device further includes verification methods, adapted to analyze the signal received on said other connection terminal, to reveal the presence or absence of a cardiac signal, and, if a cardiac signal is present on said other connection terminal, outputting an inhibition command to the switching methods in response;

The verification further includes, if a cardiac signal is present on said other connection terminal, transmitting in response an alert signal of uncertainty;

The discriminating methods include a signal level test of the collected signal, adapted to reveal the presence of a cardiac signal if the signal level collected on the connection terminal exceeds a given threshold for the duration of a predetermined detection window;

The signal level test further includes a stability test of intervals separating the successive events of said cardiac signal collected during the duration of the detection window, the stability test outputting an indicator of stability or of lack of stability. In addition, the discriminating methods are further adapted to issue an inhibition command to the switching methods if the issued indicator is an indicator of lack of stability;

The discriminating methods include comparing the levels, determined by the level test, of the signals respectively collected on the first and second connection terminals. In addition, the switching methods couple the cardiac therapy circuit to the connection terminals on which the highest signal level was collected, and couple the peripheral therapy circuit to the connection terminals on which the lowest signal level was collected;

The comparison methods of the respective signal levels further include issuing a command for inhibiting the switching methods if the difference between the respective levels of the signals collected on the first and second terminals is less than a predetermined minimum difference.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

An exemplary embodiment of the invention will now be described.

Regarding its software aspects, various embodiments of the invention may be implemented by appropriate programming of the controlling software of a known device, including a programmable microprocessor and circuits for collecting, shaping and delivering electrical signals collected by implanted electrodes, and to deliver stimulation pulses to these electrodes. It is possible to transmit to it by telemetry software that will be stored in memory and executed to implement the functions of the invention which will be described below. The adaptation of these devices to implement the functions of the invention is within the reach of a skilled-in-the-art person and will not be described in detail.

Various embodiments of the invention may be implemented primarily by software, through appropriate algorithms performed by a microcontroller or a digital signal processor. For the sake of clarity, the various processing applied will be decomposed and schematized by a number of separate functional blocks in the form of interconnected circuits, but this representation, however, is only illustrative, these circuits including common elements in practice corresponding to a plurality of functions generally performed by the same software.

Figure 1:
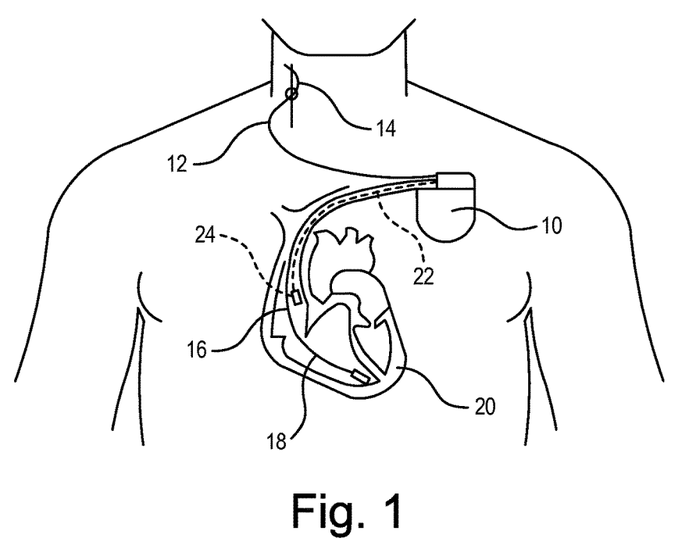
FIG. 1 is a schematic representation of various elements implemented by a device for delivering both a cardiac therapy and a peripheral therapy, according to an exemplary embodiment.

In FIG. 1, a system including an implantable generator 10 for cardiac therapy and peripheral therapy is illustrated.

The generator 10 generates stimulation pulses transmitted by a lead 12 to an electrode applied to a peripheral anatomical structure 14, such as the vagus nerve, the electrode also being possibly located close to the nerve or one of its branches. The generator 10 is also provided with detection/stimulation circuits coupled to at least one electrode of a lead 16, for example an endocardial lead provided at its distal end 18 of an electrode in contact with a wall of a heart 20.

The generator 10 may also be provided with other leads than the leads 12 and 16, for example an atrial lead 22 placed in the atrium or in the vicinity thereof and provided at its distal end 24 with a detection/stimulation electrode of the atrium.

The lead 16, or the leads 16 and 22, collects endocardial electrogram signals (EGM) representative of the patient's cardiac activity, produced by depolarization in the heart.

Note that this method to obtain an input signal representative of the patient's heart activity is not exhaustive and that other signals for implementation of the invention, (e.g., endocardial acceleration signals (EA) corresponding to the characteristic sounds of the heart and for deriving various parameters representative of cardiac activity, in particular as described in detail in EP 2092885 A1 (Sorin CRM)) can be used as an alternative or complement.

Figure 2:
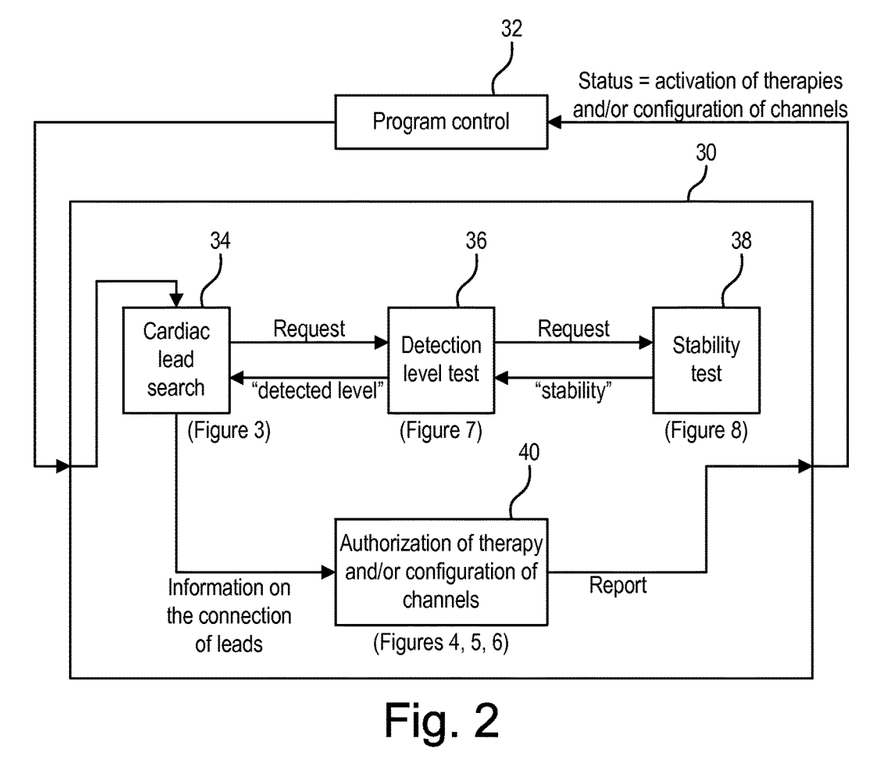
FIG. 2 illustrates as a block diagram the various functions implemented by the device, according to an exemplary embodiment.

FIG. 2 illustrates as a block diagram various functions implemented by a device within the generator 10.

One embodiment is based on the device's ability to detect cardiac signals on both a channel reserved for a cardiac therapy and on a channel reserved for a peripheral therapy. A lead implanted in the heart (such as the lead 16 or 22 in FIG. 1) will produce a cardiac signal whose level will be higher than that produced by a lead located outside the heart (such as the lead 12 of FIG. 1). The device is able to identify which lead receives the highest signal, which is the lead implanted in the heart.

According to a first embodiment, prior to allowing delivery of the therapy, the device analyzes the signal received on each of a plurality of generator terminals (e.g., terminals connected to the peripheral therapy circuit and terminals connected to the cardiac therapy circuit) for detecting a possible presence of a cardiac signal:

If the detection of a cardiac signal cannot be established on any of the terminals, it may not be possible for the device to determine which lead is implanted in the heart, and an indetermination message may be produced;

If it is possible to observe a cardiac signal on one of the two terminals, or if the level of the detected cardiac signal is substantially higher on a terminal with respect to the other, the system may conclude that the lead coupled to the terminal with the higher cardiac signal is a lead implanted in the heart;

If a cardiac signal is observed on a lead that is not connected to the terminal of cardiac therapy circuit, the device may inhibit the delivery of the peripheral therapy (and possibly also the cardiac therapy). Otherwise, cardiac and peripheral therapies will be allowed.

This principle of verification of the compatibility of the leads can be extended to a device having a plurality of cardiac therapy channels and/or several peripheral therapy channels. The verification is then operated so as to ensure that on each terminal connected to the cardiac therapy circuit the received signal is above a given level (and thus it is a cardiac signal that is present), while for each peripheral therapy terminal, the received signal is below a given threshold. If at least one of the two preceding conditions is not verified, then the delivery of cardiac and peripheral therapies may be inhibited.

According to a second embodiment, the (cardiac or peripheral) connection terminals are not assigned and may receive the connection pins of either the cardiac or peripheral leads.

The allocation of the functions of the terminals is established after self-identification of the cardiac lead. The terminal to which the cardiac lead is connected is coupled to the cardiac therapy circuitry, and the other lead is coupled to the peripheral therapy circuit. If no cardiac lead can be found, or if two cardiac leads are found, the therapy is not permitted and the device returns an "indeterminable" value as an identification parameter of the cardiac lead, a situation that will be detailed below in connection with FIG. 5.

FIG. 2 shows a block diagram of various modules for performing these functions, grouped in a module 30 operating under the control of a programming control module 32, of higher order.

Figure 3:
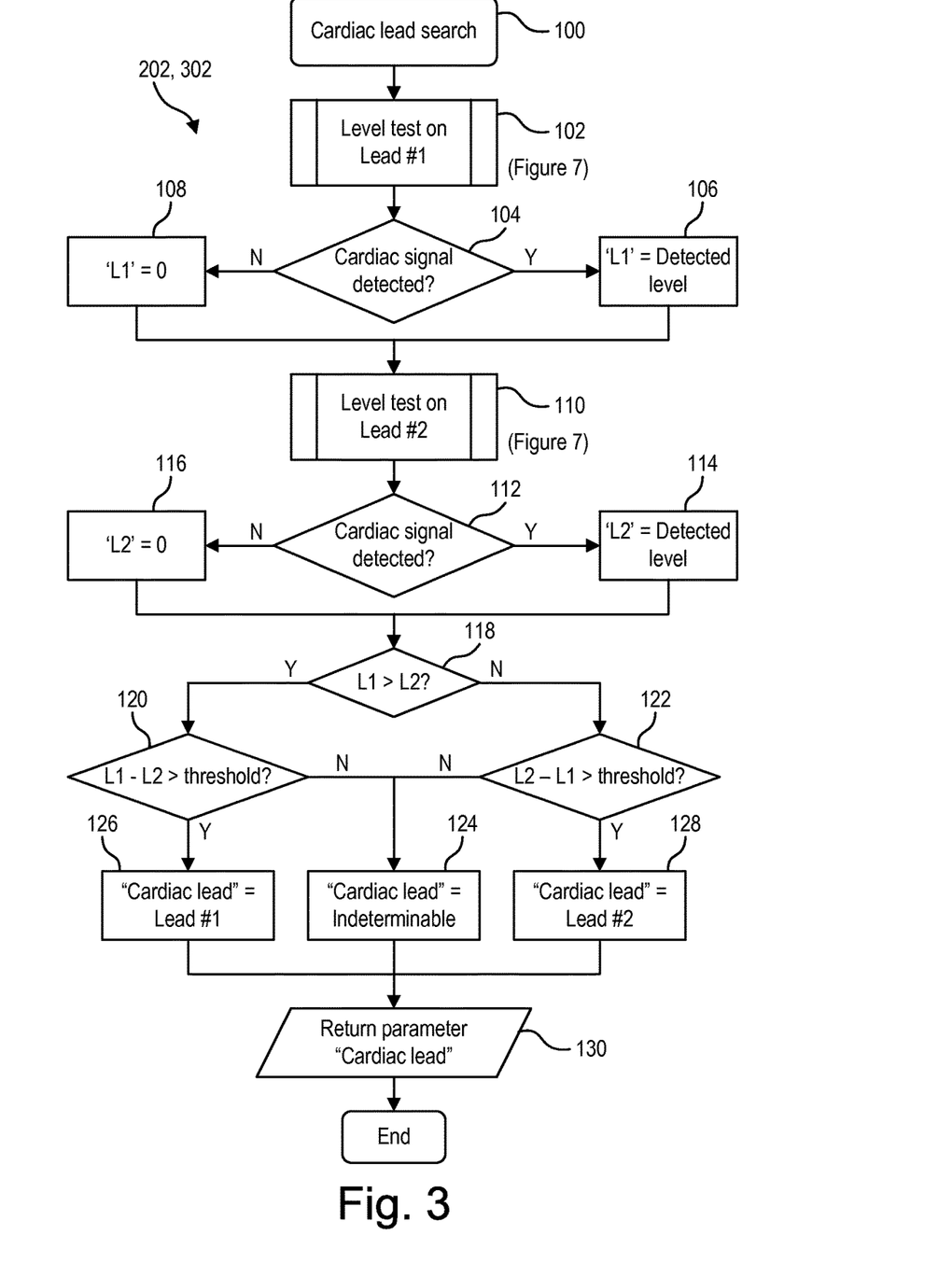
FIG. 3 is a flowchart showing one sequence of steps implemented by a search module for searching of a cardiac lead, according to an exemplary embodiment.

The control module 32 may issue a request towards the module 30, to search for the terminal to which a cardiac lead is connected (block 34, described in detail in FIG. 3).

This lead search may be executed by exchange with a detection level test module (block 36, described in detail in FIG. 7) which returns a parameter "detected level" to a cardiac lead search module 34. The detection level test module 36 uses a stability test module (block 38, described in detail in FIG. 8) to test the stability of a detected cardiac signal. The stability test module 38 returns a binary parameter "stability" to the level test module 36.

Figure 4:
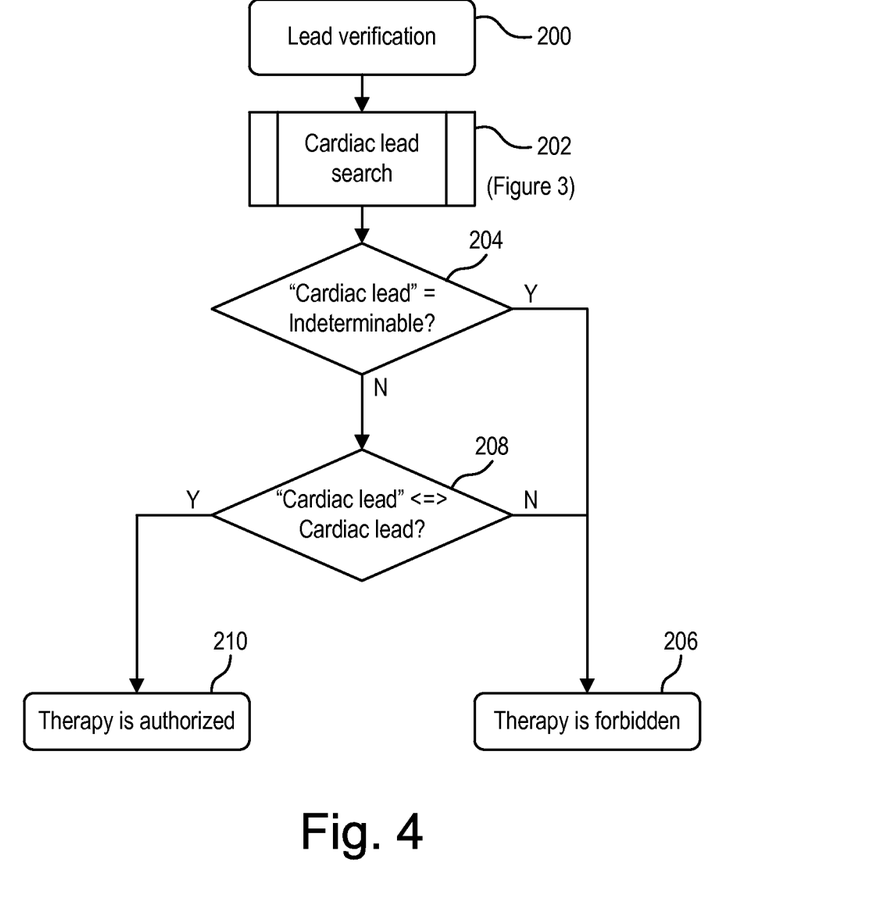
FIG. 4 is a flowchart showing one sequence of steps implemented by a verification module for verification of a compatibility of one or more leads, according to an exemplary embodiment.
Figure 5:
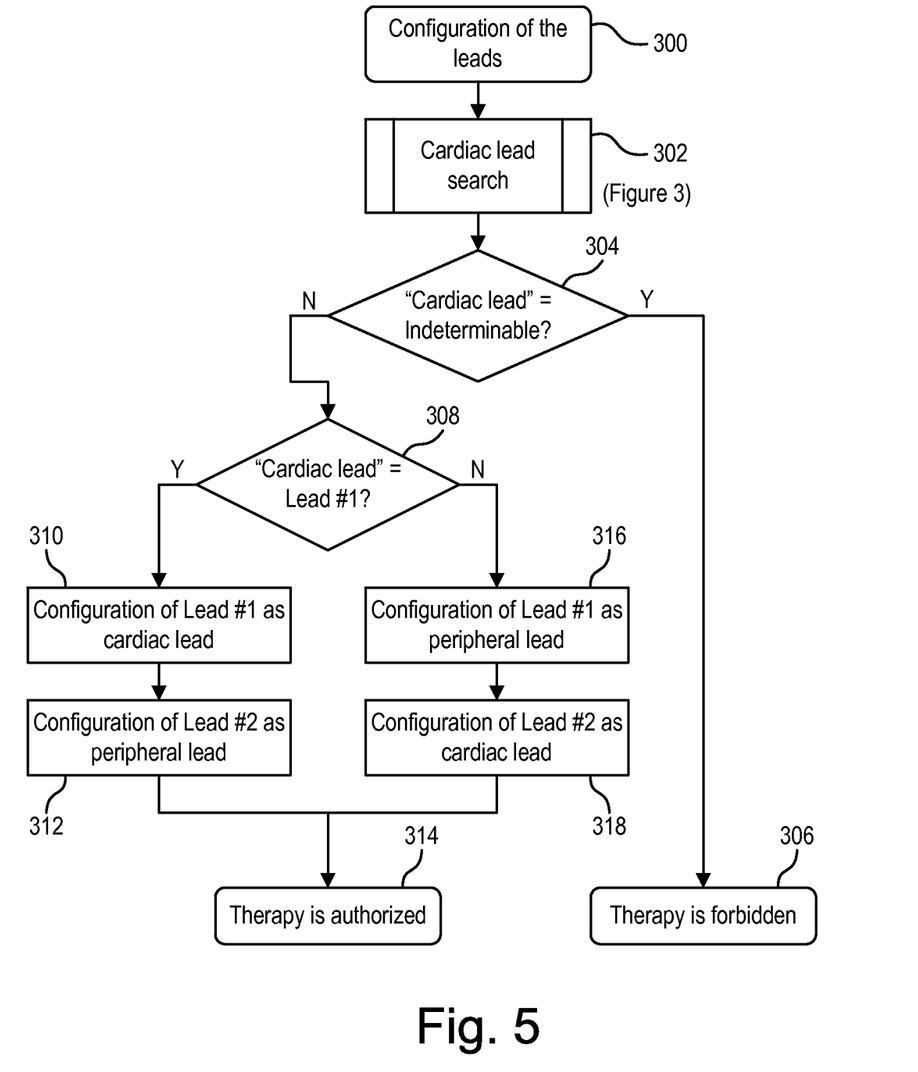
FIG. 5 is a flowchart showing one sequence of steps implemented by an automatic control module for controlling the leads providing coupling thereof to one or more terminals of one or more respective generator, according to an exemplary embodiment.
Figure 6:
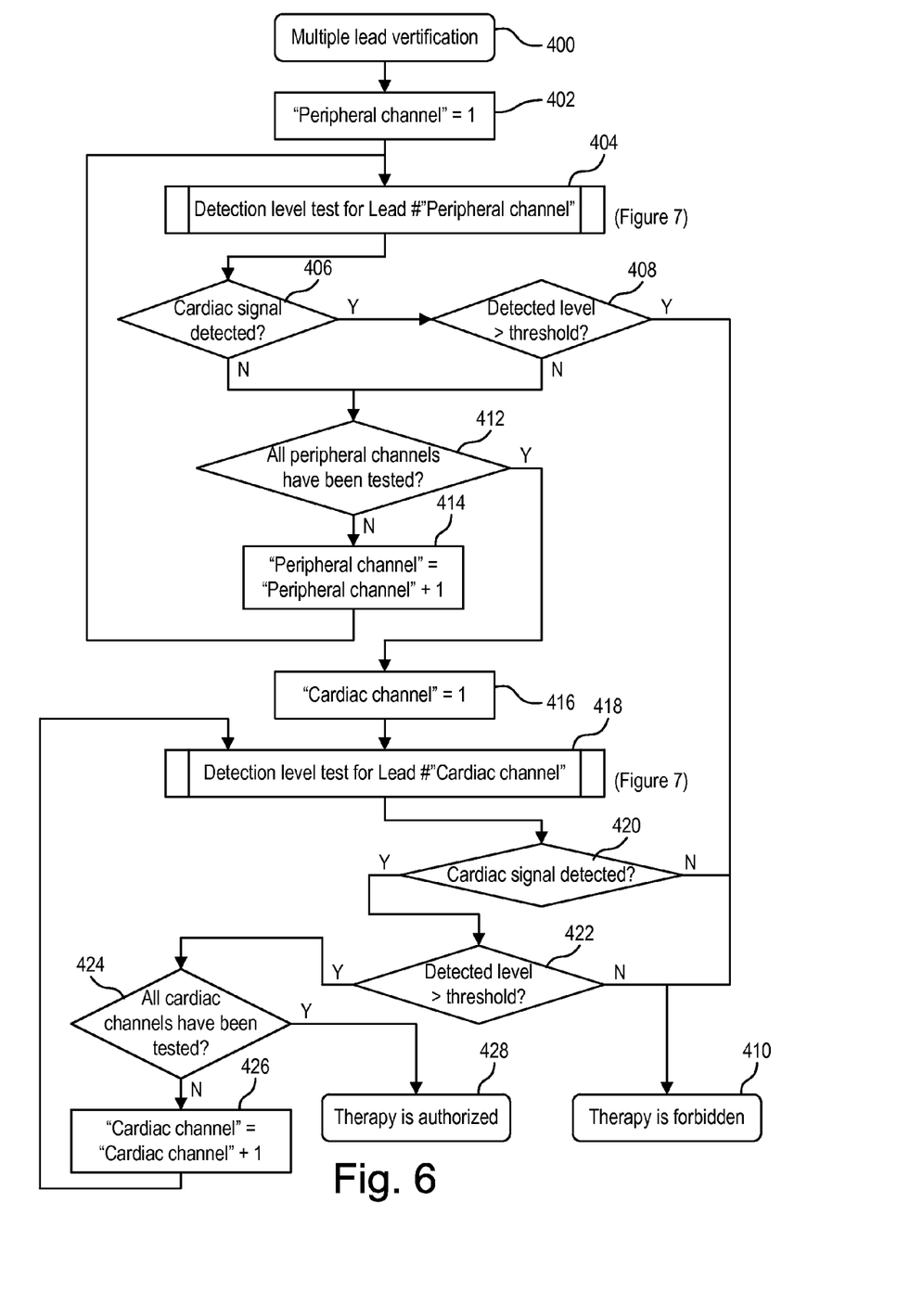
FIG. 6 is a flowchart homologous to that of FIG. 4, in the case of a plurality of leads on a cardiac and/or a peripheral terminal.

Once the terminal on which the cardiac lead is mounted has been identified (block 34), the corresponding information is transmitted to a verification module to verify the compatibility of the leads and authorize the therapy, and/or automatic configuration of the channels (block 40, described in detail in FIGS. 4, 5 and 6). The result of this operation (activation state or not of therapies, and/or channel configuration) may be returned to the control module 32 for continuing the method of starting-up the generator and determining an appropriate action.

FIG. 3 illustrates in detail the steps implemented by the cardiac lead search module 34 for the search of the cardiac lead by the device.

The call of the cardiac lead search module (block 100) triggers a first signal level test on a first of two leads (block 102, "lead #1"). The detailed method in which this level test is operated will be described below in detail with reference to the flowchart of FIG. 7.

If a cardiac signal has been detected on the lead #1 (block 104), the value of the detected level is stored in a variable (block 106, "L1"); otherwise, the variable "L1" is forced to zero (block 108).

The operations of steps 102 to 108 may be repeated in the same method for the other lead (blocks 110 to 116, "lead #2"), resulting in a second variable ("L2") representative of the detected (or not detected) signal level on the lead #2.

Determining which of the levels is the highest occurs by comparing the values of L1 and L2 (block 118). However, if the difference between the two values L1 and L2 is, in absolute value, below a given threshold (blocks 120, 122), it is determined that there is uncertainty and the test gives "indeterminable" value to a "cardiac lead" parameter (block 124). The latter case can also correspond to a situation where two cardiac leads are mistakenly connected to the generator.

If the difference between the L1 and L2 values is sufficient, the device considers that the cardiac lead is lead #1 (block 126), otherwise it is determined that the cardiac lead is lead #2 (block 128). The device returns a "cardiac lead" parameter with the value "lead #1", "lead #2" or "indeterminate" (block 130).

From the "cardiac lead" information returned by the module 34 (corresponding to the flowchart of FIG. 3), the device then operates (module 40) verification of the compatibility of leads so as to allow or inhibit the therapy delivery.

As shown in FIG. 4, this sequence is started (block 200) by a call to the cardiac lead search module 34 for the cardiac lead (block 202) described above with reference to FIG. 3. If the "cardiac lead" parameter has the "indeterminable" value (block 204), it is determined that the therapy may not be issued. The pulse generators are inhibited and an alert signal of prohibited therapy may be issued (e.g., for transmission to an external programmer) so that the practitioner can take an appropriate action in response (block 206).

If, however, a cardiac lead has been determined ("cardiac lead"="lead #1" or "lead #2"), the device verifies that the corresponding lead #1 or #2 is effectively the one that is connected to the cardiac therapy circuit terminal (block 208). If so, therapy is authorized (block 210). Otherwise, that is to say if the cardiac lead is connected to the terminal of the peripheral therapy circuit, the device does not allow the delivery of the therapy (block 206, described above).

In another embodiment of the invention, instead of checking the compatibility of the leads (i.e., determining whether the cardiac and peripheral leads have been correctly connected to the respective connection terminals), it is determined that the connection of the leads on the connector has taken an indifferent connection, the device may be in charge of identifying the leads and coupling these connections to their corresponding generators.

This alternative approach is illustrated in the flowchart of FIG. 5.

The automatic control module (block 300), which may be integrated into the module 40 of FIG. 2, operates a search of the cardiac lead (block 302), as described in detail above with reference to FIG. 3.

If the returned "cardiac lead" parameter is "indeterminate" (block 304), the therapy is prohibited in any case (block 306, similar to block 206 described above with reference to FIG. 4).

If, however, one of the two leads has been identified as a cardiac lead, for example the lead #1 (block 308), then the lead #1 is configured as a cardiac lead, (coupled to said cardiac therapy circuit) and the other lead, lead #2, is configured as a peripheral lead (coupled to the peripheral therapy circuit) (blocks 310 and 312). Otherwise, lead #1 is configured as a peripheral lead and the lead #2 is configured as a cardiac lead (blocks 316 and 318).

The leads having thus been set, the delivery of a therapy is permitted (block 314, similar to block 210 described with reference to FIG. 4).

FIG. 6 illustrates a generalization of one verification method of the leads described above with reference to FIG. 4 in the case of two leads, to any number of leads on both the cardiac channel and on the peripheral channel.

This method of checking the compatibility of a plurality of leads (block 400) includes an initialization of a counter of peripheral channels at "1" (block 402). A detection level test is performed for the lead # "peripheral channel" (block 404). This test, similar to that of blocks 102 and 110 described above, will be described in detail below with reference to FIG. 7.

If, on this lead # "peripheral channel," a cardiac signal is detected (block 406) and the level of this signal exceeds a predetermined threshold (block 408), the therapy is forbidden (block 410, similar to blocks 206 and 306 described above). Indeed, on a terminal supposed to receive a peripheral lead, an elevated cardiac signal level indicates that the lead in question was mistakenly implanted in the heart.

Otherwise, that is to say if no cardiac signal has been detected on the lead # "peripheral channel," or if the level of the detected signal is very weak, then the method is repeated for the leads connected to the other peripheral channels, iteratively (blocks 412 and 414).

Once all the peripheral channels have been explored, the method is repeated in the same way for the various cardiac channels, by the steps 416, 418, 420, 422, 424 and 426, which are homologous to the steps 402, 404, 406, 408, 412 and 414 described above.

Having explored all peripheral channels and all cardiac channels, if compatibility is confirmed, the therapy is permitted (block 428, similar to blocks 210 and 314 described above).

Figure 7:
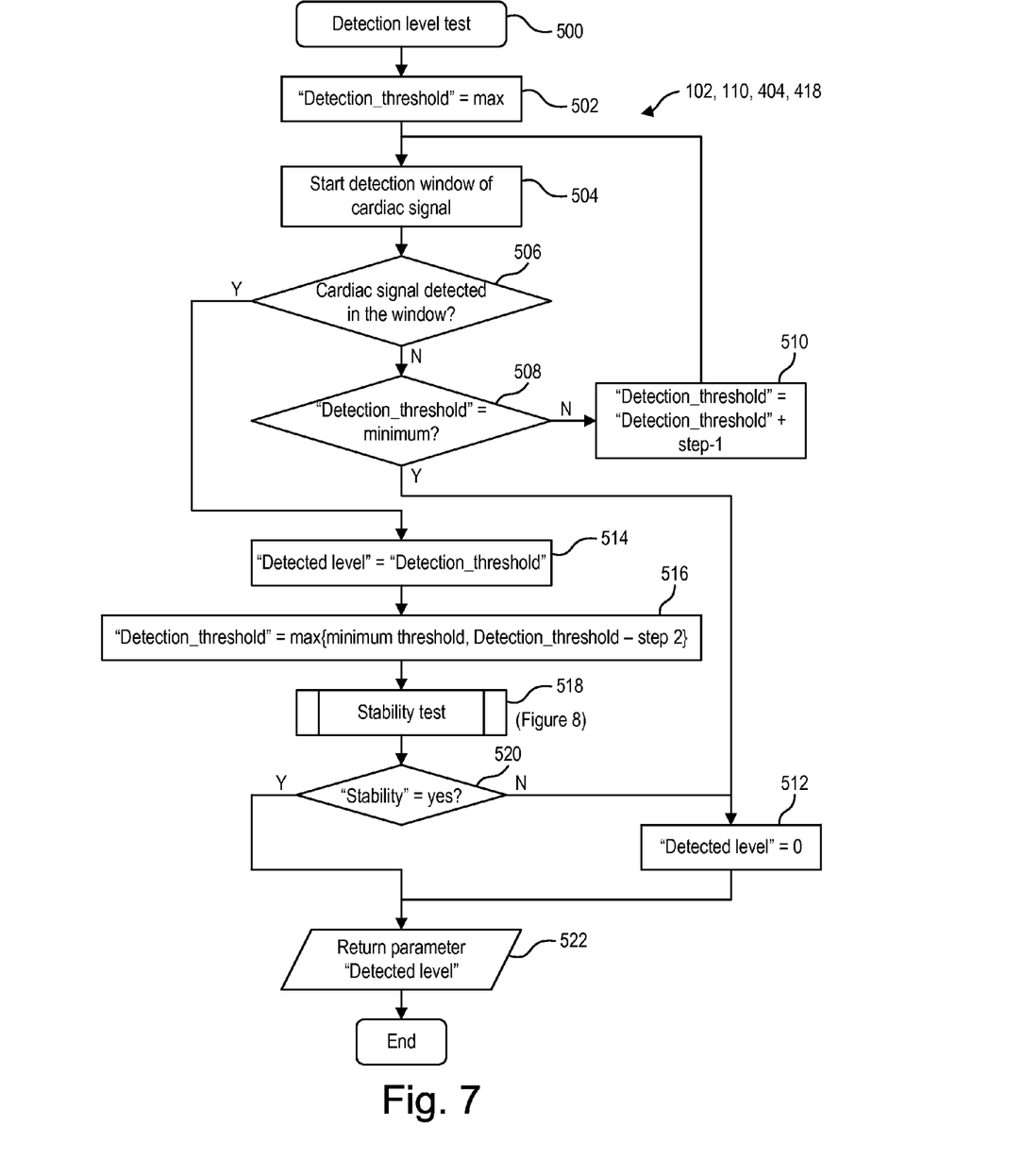
FIG. 7 is a flowchart showing one sequence of steps utilized by a test module for a test of a level of detection to recognize a presence or absence of a cardiac signal in a signal detected by the lead.

The flowchart of FIG. 7 illustrates various steps of the detection level test (block 500) of steps 102, 110, 404 and 418 of the flowcharts above.

A parameter "detection_threshold" is initialized to a predefined maximum value (block 502). A cardiac signal detection window is opened (block 504) to determine a presence or absence of a cardiac signal in the window (block 506).

If no cardiac signal is detected, the parameter "detection_threshold" is reduced by one step ("step—1"), as long as it does not reach a predetermined minimum value (blocks 508 and 510).

If, in step 508, the detection threshold has reached the predetermined minimum value, then the value "detected level" is forced to zero (block 512) and the process is terminated. This means that even with a very low threshold, it may not be possible to detect a cardiac signal, and which may be caused by the presence of a signal from a lead located on or close to a peripheral anatomical structure, and not in the heart.

If, at step 506, a cardiac signal is observed, the value of "detection_threshold" is stored in a parameter "detected level" (block 514), and "detection_threshold" is forced to a value equal to the highest value either of the minimum or of the present "detection_threshold" value reduced by one step ("step 2") (block 516).

The process performs a stability test of heart rate, hereinafter described in detail with reference to FIG. 8 (block 518). If stability is determined (block 520), the test returns the "detected level" parameter determined according to the process (block 522).

If, in step 520, the heart rate stability is not determined, then the "detected level" parameter is set to zero (block 512). Although a signal of higher level than the detection threshold is detected, this signal is not stable, which indicates a suspected problem, which must be taken into account.

Figure 8:
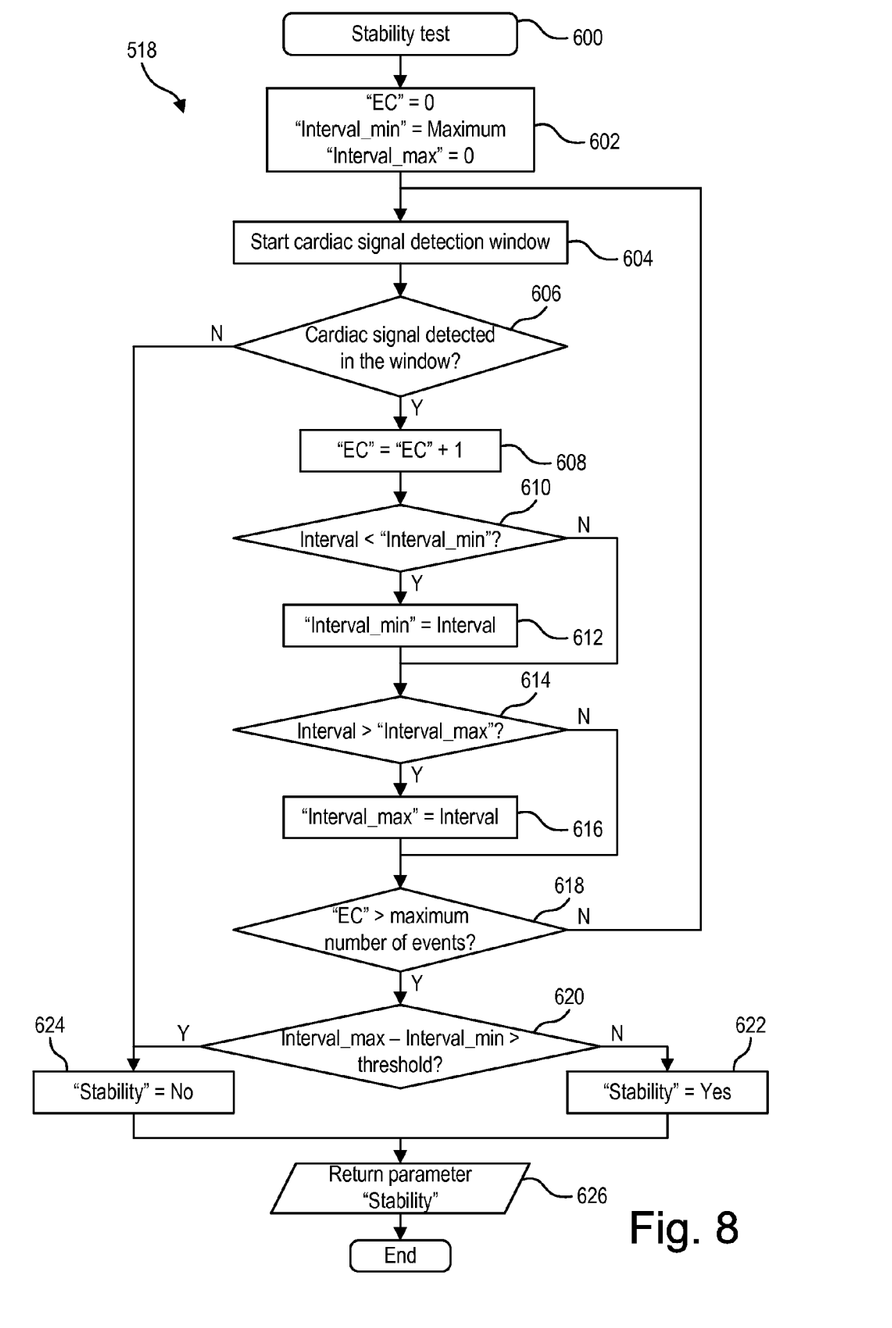
FIG. 8 is a flowchart showing one sequence of steps implemented by a stability module for a stability test of the cardiac signal detected by the test module for testing the detection level.

FIG. 8 illustrates the various steps of the stability test (block 600) mentioned above in step 518 of FIG. 7.

A number of parameters are initialized (block 602), namely a counter of events "EC" initialized to zero, a minimum interval parameter "interv_min" initialized to a predefined maximum value, and a maximum interval parameter "interv_max" initialized to zero.

A cardiac signal detection window is opened (block 604) for detecting the presence of a cardiac signal in the window (block 606). When the signal is detected (e.g., a P-wave) the event counter "EC" is incremented by one (block 608) and the measured interval is compared with the limits "interv_min" and "interv_max" and forced to one or the other of these values if the limit is reached (blocks 610, 612, 614 and 616).

The method may be repeated iteratively until a predetermined maximum number of events (block 618) is reached.

The iterated steps 610 to 616 operate a search of the minimum and of the maximum of the range of all the successive detected events, the minimum/maximum value may be optionally updated to each event, with respect to the previous event.

If the difference between the maximum interval "interv_max" and the minimum interval "interv_min" is less than a predetermined threshold (block 620), it is considered that the rate is stable and the value "yes" is given to the "stability" parameter (block 622). Otherwise, the value "no" is given to the "stability" parameter (block 624). This "stability" parameter is then returned to the test module of the detection level (module 36 of FIG. 2, the method is explained in FIG. 7), for continued operation.

What is claimed is:

1. An active implantable medical device comprising:
a cardiac therapy circuit configured to generate stimulation, defibrillation and/or resynchronization pulses;
a peripheral therapy circuit configured to generate peripheral stimulation pulses;
first and second connection terminals, each adapted to receive either a first lead or a second lead;
wherein one of the leads is a cardiac detection/stimulation lead and the other is a peripheral detection/stimulation lead; and
a processor configured to determine a respective connection configuration of the leads to the first and second connection terminals and selectively activate or inhibit the cardiac and peripheral therapy circuits by:
collecting a signal on the first connection terminal and the second connection terminal;
analyzing the signals to detect whether a cardiac signal is present by conducting a level test by collecting signals on the first and second connection terminals during a predetermined detection window, wherein the level test comprises detecting whether a cardiac signal is present on the terminal when a level of the signal on the corresponding terminal exceeds a given threshold;
conducting a level comparison, wherein the level comparison is a calculation of a difference between the levels of the signals respectively collected on the first and second terminals detected by the level test;
coupling the cardiac therapy circuit to the connection terminal wherein a high signal level was collected;
coupling the peripheral therapy circuit to the connection terminal wherein a low signal level was collected;
selectively activating the cardiac therapy circuit and peripheral therapy circuit when the presence of the cardiac signal is detected on the first connection terminal or the second connection terminal; and
selectively inhibiting the cardiac therapy circuit and peripheral therapy circuit when the presence of a cardiac signal is not detected on the first connection terminal or the second connection terminal.

2. The device of claim 1, wherein the processor is further configured to emit an alert signal when the cardiac therapy circuit and the peripheral therapy circuit are inhibited.

3. The device of claim 1, wherein the processor is further configured to emit a confirmation signal when the cardiac therapy circuit and the peripheral therapy circuit are activated.

4. The device of claim 1, wherein the level test further comprises a stability test evaluating a plurality of intervals between successive events of the signal collected during the duration of the predetermined detection window when a cardiac signal is present, wherein the stability test outputs an indicator of stability or absence of stability; and the processor is further configured to supply an inhibition command to the cardiac therapy and peripheral therapy circuits when the indicator is an indicator of absence of stability.

5. A medical device comprising:
a cardiac therapy circuit configured to generate stimulation, defibrillation and/or resynchronization pulses;
a peripheral therapy circuit configured to generate peripheral stimulation pulses;
first and second connection terminals, each adapted to receive either a first lead or a second lead, wherein the first connection terminal is coupled to the cardiac therapy circuit and the second connection terminal is coupled to the peripheral therapy circuit;
wherein one of the leads is a cardiac detection/stimulation lead and the other is a peripheral detection/stimulation lead; and
a processor configured to verify a respective connection configuration of the leads to the first and second connection terminals and selectively activate or inhibit the cardiac and peripheral therapy circuits by:
collecting a signal on the first connection terminal;
analyzing the signal to detect whether a cardiac signal is present;
collecting a second signal on the second connection terminal;
analyzing the second signal to detect whether a cardiac signal is present, wherein:
analyzing the signal and the second signal to detect whether a cardiac signal is present comprises conducting a level test by collecting signals on the first and second connection terminals during a predetermined detection window,
the level test comprises detecting whether a cardiac signal is present on the terminal when a level of the signal on the corresponding terminal exceeds a given threshold,
the level test further comprises a stability test evaluating a plurality of intervals between successive events of the signal collected during the duration of the predetermined detection window when a cardiac signal is present, wherein the stability test outputs an indicator of stability or absence of stability, and
the processor is further configured to supply an inhibition command to the cardiac therapy and peripheral therapy circuits when the indicator is an indicator of absence of stability;
selectively activating the cardiac therapy circuit and peripheral therapy circuit when the presence of the cardiac signal is detected on the first connection terminal and the presence of a cardiac signal is not detected on the second connection terminal; and
selectively inhibiting the cardiac therapy circuit and peripheral therapy circuit when at least one of the following occurs: the presence of a cardiac signal is not detected on the first connection terminal, the presence of the cardiac signal is detected on the second connection terminal, or the inhibition command is received by the cardiac therapy and peripheral therapy circuits.

6. The device of claim 5, wherein the processor is further configured to emit an alert signal when the cardiac therapy circuit and the peripheral therapy circuit are inhibited.

7. The device of claim 5, wherein the processor is further configured to emit a confirmation signal when the cardiac therapy circuit and the peripheral therapy circuit are activated.

8. The device of claim 5, wherein the processor is further configured to:
conduct a level comparison, wherein the level comparison is a calculation of a difference between the levels of the signals respectively collected on the first and second terminals detected by the level test;
couple the cardiac therapy circuit to the connection terminal wherein a high signal level was collected; and
couple the peripheral therapy circuit to the connection terminal wherein a low signal level was collected.

9. A method of discriminating between and activating a plurality of leads, the method comprising:
verifying a terminal connection configuration of the plurality of leads to a first and a second connection terminals, wherein the terminal connection configuration is verified by:
collecting a signal on the first connection terminal;
analyzing the signal to detect whether a cardiac signal is present;
collecting a second signal on the second connection terminal; and
analyzing the second signal to detect whether a cardiac signal is present, wherein analyzing the signal and the second signal to detect whether a cardiac signal is present comprises conducting a level test by collecting signals on the first and second connection terminals during a predetermined detection window, wherein the level test comprises detecting whether a cardiac signal is present on the terminal when a level of the signal on the corresponding terminal exceeds a given threshold;
conducting a level comparison, wherein the level comparison is a calculation of a difference between the levels of the signals respectively collected on the first and second terminals detected by the level test;
coupling the cardiac therapy circuit to the connection terminal wherein a high signal level was collected; and
coupling the peripheral therapy circuit to the connection terminal wherein a low signal level was collected;
selectively activating a cardiac therapy circuit and peripheral therapy circuit when the presence of a cardiac signal is detected on the first connection terminal or the second connection terminal and the presence of a cardiac signal is not detected on the other of the first connection terminal or the second connection terminal; and
selectively inhibiting the cardiac therapy circuit and peripheral therapy circuit when at the presence of a cardiac signal is not detected on the first connection terminal or the second connection terminal.

10. The method of claim 9, further comprising:
emitting an alert signal when the cardiac therapy circuit and the peripheral therapy circuit are inhibited.

11. The method of claim 9, further comprising:
emitting a confirmation signal when the cardiac therapy circuit and the peripheral therapy circuit are activated.

12. The device of claim 9, wherein the level test further comprises a stability test evaluating a plurality of intervals between successive events of the signal collected during the duration of the predetermined detection window when a cardiac signal is present, wherein the stability test outputs an indicator of stability or absence of stability; and the processor is further configured to supply an inhibition command to the cardiac therapy and peripheral therapy circuits when the indicator is an indicator of absence of stability.

* * * * *